United States Patent [19]

Chiba et al.

[11] Patent Number: 5,302,507
[45] Date of Patent: Apr. 12, 1994

[54] ANTIGENIC PEPTIDE FOR DETECTING ANTI-HEPATITIS C VIRUS ANTIBODIES AND USE THEREOF

[75] Inventors: Joe Chiba, B-26-4, 626, Endo, Fujisawa-shi, Kanagawa-ken; Tatsuo Miyamura, Tokyo; Izumu Saito, Tokyo; Shizuko Harada, Tokyo; Yoshiharu Matsuura, Kamifukuoka, all of Japan

[73] Assignees: Japan as represented by Director General of the Agency of the National Institute of Health, Tokyo; Joe Chiba, Fujisawa, both of Japan

[21] Appl. No.: 744,427

[22] Filed: Aug. 13, 1991

[30] Foreign Application Priority Data

Aug. 14, 1990 [JP] Japan .................. 2-214553

[51] Int. Cl.$^5$ .................. C12Q 1/70; C07K 7/08
[52] U.S. Cl. .................. 435/5; 530/326; 436/820
[58] Field of Search .................. 435/5; 530/326; 436/820

[56] References Cited

U.S. PATENT DOCUMENTS 4,673,634  6/1987  Seto et al. .................. 435/5
5,106,726  4/1992  Wang .................. 435/5

FOREIGN PATENT DOCUMENTS 0388232  3/1990  European Pat. Off. ...... C12N 15/51

OTHER PUBLICATIONS

Chiba et al., Proc. Natl. Acad. Sci. 88:4641–45 (1991).
Harada et al., J. Virology 65:3015–3021 (1991).
Kato et al., Jpn J Cancer Res 81:1092–1094 (1990).
Muraiso et al., Biochem Biophys. Res. Comm. 172:511–516 (1990).

*Primary Examiner*—Christine M. Nucker
*Assistant Examiner*—M. P. Woodward
*Attorney, Agent, or Firm*—Oblon, Spivak, McClelland, Maier & Neustadt

[57] ABSTRACT

The antigenic peptide represented by the following amino acid sequence (SEQ ID NO: 1)

Met—Ser—Thr—Asn—Pro—Lys—Pro—Gln—Arg—Lys—
Thr—Lys—Arg—Asn—Thr—Asn—Arg—Arg—Pro—Gln and a method of the detection of anti-HCV antibodies wherein the above peptide is brought into contact with a sample under the conditions that the peptide is bound to anti-HCV antibodies present in the sample to form an immunological complex and the formation of the immunological complex is measured to confirm the existence of the anti HCV antibodies in the sample. The method is highly specific and sensitive to anti-HCV antibodies.

3 Claims, No Drawings

ANTIGENIC PEPTIDE FOR DETECTING ANTI-HEPATITIS C VIRUS ANTIBODIES AND USE THEREOF

DESCRIPTION OF THE INVENTION

This invention relates to an antigenic peptide relating to a virus which causes serum hepatitis which is not hepatitis A or B, in particular a virus which causes hepatitis C (hepatitis C virus (HCV)), and a diagnostic reagent for detecting an antibody against HCV.

BACKGROUND OF THE INVENTION

There are known some types of viruses which cause viral hepatitis. Hepatitis A virus is an RNA virus having a diameter of 27 nm which belongs to picornavirus and causes epidemic hepatitis through oral infection (Fineston, S. M. et al., Science, 182: p. 1026, 973). Hepatitis B virus is a DNA virus having a diameter of 42 nm which belongs to hepadnavirus and causes hepatitis through blood infection (Dane, O. S. et al., Lancet. I: p. 241, 1974) For these viruses, definite diagnostic methods and prevention measures have been established.

A hepatitis virus which does not belong to any of the above types was called non-A, non-B hepatitis virus. Recently, it has been known that there are two kinds of non-A, non-B hepatitis viruses. One is calicivirus like hepatitis virus having a diameter of 27 to 32 nm and causing epidemic hepatitis through oral infection in India, Myanma, Afghanistan, north Africa and etc. (Khuroo, M. S. Am. J. Med.,68: p. 818-824, 1980). This was named Hepatitis E virus (HEV) for "E" of epidemic or enteric.

The other is a virus which causes most of hepatitis after blood transfusion and which is called hepatitis C virus. The existence of the virus has been known for a long time (Tabor, E. et al., Lancet. I: p. 463, 1978) but the virus itself has not been made sufficiently clear in spite of many efforts by researchers throughout the world.

Under such circumstances, Choo, Q. et al. of the United States succeeded in cloning of cDNA of HCV in 1989 and reported that they established a system for the detection of anti-HCV antibodies using an expressed protein encoded by a part of the cDNA (Choo, Q. et al., Science, 224, p. 359-362, 1989; Kuo, G. et al., Science 224, p. 362-364, 1989). On the other hand, the inventors of the present invention independently have succeeded in cloning of cDNA coding for HCV structural protein region using high GPT plasma of a Japanese blood donor and have filed a patent application World Intellectual Property Organization International Publication No. WO 91/04262.

An ELISA system for the detection of anti-HCV antibodies prepared by Kuo, G. et al. (HCV Ab ELISA kit manufactured by Ortho Inc.) uses as an antigen a protein which is expressed in a yeast as a fused protein between superoxide dismutase (SOD) and a part called C100 of NS3 to NS4 region which is considered non-structural region of the virus gene. This system can detect specifically and sensitively antibodies against virus in patients infected with HCV and is highly valuable as a judging measure in screening of blood for transfusion which could spread hepatitis C after blood transfusion. However, anti-C100 antibody measured in the above-mentioned antibody detection system causes positive reaction after the symptoms of hepatitis C is shown but cannot be detected usually from 3 to 6 months after the infection, during which the system cannot be used as a diagnostic measure for hepatitis C. This is one of the biggest problems of the system. Even if only blood which is negative in anti-C100 antibody test using the system is transfused, hepatitis C breaks out to some extent. It is, therefore, considered that the antibody test using the system could detect and exclude about 50% of post-tranfusion hepatitis. Thus, there is a strong need for a new method for detecting the antibody. Further, the following problems still remain unsolved in a detection system using a fused protein virus antigen produced by a recombinant DNA technique.

1) There is a possibility of decomposition of desired expressed protein by proteases derived from a recombinant microorganism which produced the protein.
2) Many and complicated processes are required to purify desired antigenic protein from a large amount of proteins derived from a cultured recombinant microorganism, supernatant of a cultured cell, or cell body.
3) There is a possibility of non specific reaction caused by a fused protein or a recombinant microorganism used for the expression.
4) Since it is essential to culture a recombinant microorganism, lot-to-lot variation is apt to occur.

The above-mentioned commercially available system for the detection of anti-HCV antibodies is very significant because it can detect rapidly and easily antibodies against hepatitis C virus, which has never been successful. However, there is a need for a diagnostic method with "100% accuracy" wherein a detection rate is improved and a non-specific reaction is inhibited. From the point of quality control, there is room for improvement. For these purposes, further researches and developments are now carried out.

The inventors of the present invention prepared a synthetic peptide of the structural region encoded by independently cloned cDNA and developed some systems for the detection of antibodies using the peptide so that it is possible to avoid non-specific reaction caused by a fused protein, non-specific reaction caused by a transformant used for the expression of the protein, or difficulty of quality control. As a result, they have accomplished the present invention.

SUMMARY OF THE INVENTION

A first object of the present invention is to provide a novel peptide which corresponds to antigeninc HCV protein and which can be used for the detection and diagnosis of HCV infection with excellent specificity, selectivity and sensitivity.

A second object of the present invention is to provide a method of the detection of anti-HCV antibodies directly using the peptide or a part thereof.

The inventors of the present invention cloned cDNA from plasma having abnormal values of liver functions (GOT and GPT) donated by a Japanese who was believed to be infected with non-A, non-B hepatitis, the details of which are disclosed in World Intellectual Property Organization International Publication No. WO 91/04262 the disclosure of which is totally incorporated herein by reference.

The inventors of the present invention inserted the cDNA into a plasmid, incorporated the recombinant plasmid into an appropriate host to express a product, purified the product and used the purified product to develop a system for the detection of anti-HCV antibodies. Separately, they deduced the sequence of the cDNA to synthesize a peptide and used the synthesized peptide to develop a system for the detection of anti-HCV antibodies.

First, in order to accomplish the first object of the present invention, they prepared the following peptide (SEQ ID NO: 1) (hereinafter referred to as Peptide-0) with a peptide synthesizer using the sequence information of the cDNA.

Met—Ser—Thr—Asn—Pro—Lys—Pro—Gln—Arg—Lys—
Thr—Lys—Arg—Asn—Thr—Asn—Arg—Arg—Pro—Gln

The second object of the present invention is accomplished by a method of the detection of anti-HCV antibodies wherein an antigenic peptide consisting of Peptide-0, a peptide containing Peptide-0 or a part of Peptide 0 is brought into contact with a sample under the conditions that the peptide is bound to anti HCV antibodies possibly present in the sample to form an immunological complex and the formation of the immunological complex is measured to confirm the existence of the anti-HCV antibodies in the sample.

Thus, the present invention is based on the discovery of a peptide antigen corresponding to a nucleoprotein in the structural region of polyprotein encoded by the HCV gene. The peptide is useful as an antigen used in a diagnostic method of HC patients caused by HCV infection or in a screening method of the exposure to HCV in blood and formulations, with high reliability and high specificity and with minimum error results.

DETAILED DESCRIPTION OF THE INVENTION

The present invention relates to an antigenic peptide corresponding to a part of the protein encoded by the HCV gene, more specifically a peptide consisting of 1 to 20 amino acids corresponding to a part of a nucleoprotein of the structural region. These novel peptides are useful for the diagnosis of HCV infection and exposure to viruses. The peptides of the present invention include oligopeptides containing amino acid sequences including a sequence which constitutes a sequential epitope which reacts with antibodies specific to HCV.

Thus, the peptides of the present invention are those having immunological reactivity concerning HCV and can be prepared by conventional solid phase peptide synthesis. One or two amino acids which are not contained in the sequence of the original protein may be added to terminal amino or carboxyl group of the peptide of the present invention. The addition of such amino acid makes it possible to bind the peptide of the invention to a carrier protein or a support. Amino acids useful for such purposes include tyrosine, lysine, glutamic acid, aspartic acid, cysteine and derivatives thereof. It is also possible to add a means binding the peptide of the invention to other proteins or peptide molecules or a support by acetylation of terminal amino group or amidation of terminal acid group using conventional methods for protein modification.

Desired peptides thus synthesized are purified in conventional purification methods and recovered. For example, synthetic peptides are generally purified by high performance liquid chromatography (HPLC) using a column for the purification of synthetic peptides, recovered, freeze-dried and used for a method of the determination of antibodies mentioned below.

These peptides can be used as an antigen in a method of the detection of antibodies against HCV antigens or HCV associating-binding antigens. In a method wherein the peptides of the invention are used to detect the existence of antibodies specific to HCV, it is preferred that the peptides are brought into contact with a sample under such conditions that the peptides react with the HCV antibodies to form immunological complex (antigen-antibody complex). The formation of such antigen-antibody complex, even if it is in a slight amount, means the existence of the HCV antibodies in the sample which can be detected and determined by suitable methods.

Such methods include enzyme-linked immunosorbent assay (ELISA), radio immuno assay (RIA), western blotting technique or other various methods using support aggregation reaction. Among them, ELISA is suitable for rapid and large scale clinical screening of serum of patients, blood for transfusion or blood derivatives.

Preferred embodiments of the present invention include those disclosed in Example 1 mentioned later and the specific embodiments which will now be explained with reference to ELISA.

The synthetic peptide is dissolved in a suitable buffer, for example, PBS (phosphate-buffered saline), transferred to each well of an ELISA plate and maintained at 4° C. for one night to permit the synthetic peptide to adsorb onto the surface of the wells. The wells are washed with PBS containing 0.05% Tween 20 (PBST). One % BSA (bovine serum albumin) in PBS is transferred to each of the wells and maintained at 37° C. for one hour to block excess protein binding sites. The wells are washed with, for example, PBST. Samples to be examined are diluted, transferred to each of the wells and maintained at 37° C. for one hour. Again, the wells are washed with PBST. Into each well HRP (horseradish peroxidase) conjugate anti-human IgG solution is added and reacted at 37° C. for one hour. After the wells are washed with PBST, an OPD (ortho-phenylene diamine) substrate solution is added and maintained at room temperature in a dark place to color-develop. After 30 minutes, 2M sulfuric acid is added to stop the reaction and absorbance at 492 nm is measured.

A synthetic peptide, Peptide 0, is used to prepare an ELISA system which shows high specificity to non-A, non-B hepatitis and high detection rate of antibodies in patients infected with non-A, non-B hepatitis. In particular, this ELISA system makes it possible to detect antibodies with a high rate from patients infected with non-A, non-B hepatitis, which have never been detected by conventional HCV Ab ELISA kit (available from Ortho Inc.).

The above embodiment has been described with reference to mainly a case where only a chemically synthesized peptide is used. However, the present invention is not limited to the embodiment. It is also possible to use a peptide containing Peptide-0 or a peptide consisting of a part of Peptide-0 to construct a suitable detection system for anti-HCV antibodies.

The ELISA systems using the polypeptides of the present invention have the following advantages over conventional and commercially available ELISA systems using antigens produced by recombinant microorganisms or cultured cells.

Construction of expression plasmids, preparation of recombinant microorganisms, cloning and experiments for the expression are not required. Further, culturing of recombinant microorganisms is not required. Consequently, there is no lot-to-lot variation and no possibility of decomposition of expressed proteins by proteases produced by cultured recombinant microorganisms.

As mentioned earlier, if desired antigenic proteins are separated from supernatants of cultured recombinant microorganisms or cultured cells, or cell bodies, many and complicated processes are required because the supernatants, or cell bodies contain a large amount of proteins other than the desired proteins. On the contrary, a method for the synthesis of a synthetic peptide with a peptide synthesizer is now almost automatized and purification of a peptide can be made on HPLC without difficulty. Further, there is no possibility of contamination by proteins derived from recombinant microorganisms, cultured cells or culture media which could cause non-specific reaction; and denaturation or inactivation of expressed proteins attendant upon purification processes.

Moreover, quality control is easy because of no lot-to-lot variations attendant upon culturing or purification processes.

The HCV antigenic peptides of the present invention are prepared on the basis of cDNA of an HCV strain which is a major one in Japan so that they can detect antibodies which cannot be detected by conventional and commercially available kits. Further, the antibody detection system of the present invention can detect antibodies at an earlier stage than conventional and commercially available kits detect, which demonstrates further advantage of the present invention.

The present invention will now be described in more detail with reference to Working Examples to which the present invention is not limited.

EXAMPLE 1

According to the sequence information of HCV cDNA separated from concentrated plasma of a Japanese World Intellectual Property Organization International Publication No. WO 91/04262, Peptide-0 was synthesized with a peptide synthesizer (430A Peptide Synthesizer manufactured by Applied Biosystems Inc.) and purified on an HPLC column for the purification of a synthetic peptide (Aquapore Prep-10, C-8, 300A pore size, 20 μm spherica silica, 10 mm ID×250 mm, available from Applied Biosystems Inc.). Conventional composition analysis of the synthetic peptide thus purified showed that the peptide was desired one. Peptide-0 was dissolved in PBS (0.1M phosphate-buffered saline) to make a concentration of 1μg/ml, 200 μl of which was transferred to each well of an ELISA plate and maintained at 4° C. for one night to permit the synthetic peptide to adsorb onto the surface of the wells. The wells were washed with PBS containing 0.01% Tween 20 (PBST). 250 μl of 0.1% BSA (Bovine serum albumin) solution in pBS was transferred to each of the wells and post-coated. Then, 200 μl of 0.1% BSA solution in PBST was transferred to each of the wells and 20 μl of plasma samples was added, lightly agitated with a plate mixer and maintained at 37° C. for one hour.

The wells were washed with PBST and then, 200 μl of HRP conjugate anti-human IgG solution were added to each of the wells and reacted at 37° C. for one hour.

After the wells were washed with PBS-T, 200 μl of a TMBZ (3,3',5,5'-Tetramethylbenzidine hydrochloride) substrate solution was added to each of the wells and reacted at 37° C. After 30 minutes, 2M sulfuric acid was added to stop the reaction. Absorbance was measured at 450 nm and 650 nm by Emaxprecision microplate reader (manufactured by Molecular Device Inc.).

The plasma samples used in this example were HCV Ab ELISA kit positive sample (Anti-C100 antibody positive) commercially available from Ortho Inc. which is widely used in the world; HCV Ab ELISA kit negative sample (Anti-C100 antibody negative) commercially available from Ortho Inc.; anti-hepatitis B virus antibody positive sample (HBV+) (negative control); and anti-hepatitis A virus antibody positive sample (HAV+) (negative control) and ten samples each were measured.

For comparison, measurement was also conducted for an assay system using a polypeptide (HCV-SF9) produced by an expression system using Baculovirus vector into which HCV cDNA discovered by the inventors of the present invention was incorporated. The results are shown in Table 1 wherein numerical values are OD values in ELISA.

TABLE 1

| No. | HCV-SF9 | Peptide-0 |
|---|---|---|
| Sample: Anti-C100 antibody positive | | |
| 1 | 0.497 | 0.745 |
| 2 | 0.720 | 0.857 |
| 3 | 0.084 | 0.122 |
| 4 | 0.694 | 1.162 |
| 5 | 0.384 | 0.154 |
| 6 | 0.710 | 0.875 |
| 7 | 0.134 | 0.180 |
| 8 | 0.418 | 0.230 |
| 9 | 0.398 | 0.499 |
| 10 | 0.522 | 0.678 |
| Sample: Anti-C100 antibody negative | | |
| 1 | 0.017 | 0.099 |
| 2 | 0.267 | 0.957 |
| 3 | 0.656 | 1.137 |
| 4 | 1.357 | 1.573 |
| 5 | 0.138 | 0.271 |
| 6 | 0.509 | 0.933 |
| 7 | 0.294 | 0.070 |
| 8 | 0.321 | 0.767 |
| 9 | 0.247 | 0.449 |
| 10 | 0.361 | 0.219 |
| Sample: Anti-HBV + | | |
| 1 | 0.036 | 0.179 |
| 2 | 0.025 | 0.067 |
| 3 | 0.033 | 0.101 |
| 4 | 0.080 | 0.160 |
| 5 | 0.023 | 0.061 |
| 6 | 0.021 | 0.057 |
| 7 | 0.078 | 0.091 |
| 8 | 0.030 | 0.056 |
| 9 | 0.057 | 0.144 |
| 10 | 0.066 | 0.125 |
| Sample: Anti-HAV + | | |
| 1 | 0.086 | 0.278 |
| 2 | 0.042 | 0.081 |
| 3 | 0.101 | 0.203 |
| 4 | 0.065 | 0.122 |
| 5 | 0.085 | 0.188 |
| 6 | 0.074 | 0.187 |
| 7 | 0.104 | 0.186 |
| 8 | 0.712 | 1.020 |
| 9 | 0.078 | 0.114 |
| 10 | 0.049 | 0.102 |

The results show that the detection system of the present invention judged eight among ten of C100 antibody positive samples to be positive. This demonstrates that the detectability of the system of the present invention is almost equal to that of HCV Ab ELISA kit commercially available from Ortho Inc. Further, the detection system of the present invention judged eight among ten of C100 antibody negative samples, to be positive, which cannot be detected by HCV Ab ELISA kit commercially available from Ortho Inc. This demonstrates remarkable advantage of the present invention over the conventional system. It is believed that the advantage stems from the difference in gene regions coding for antigenic peptides used in the ELISA systems.

Met—Ser—Thr—Asn—Pro—Lys—Pro—Gln—Arg—Lys—
Thr—Lys—Arg—Asn—Thr—Asn—Arg—Arg—Pro—Gln.

2. A kit for the detection of anti-HCV antibodies, comprising an antigenic peptide consisting of the amino sequence (SEQ ID NO: 1):

---

What is claimed is:

1. A peptide consisting of the amino acid sequence (SEQ ID NO: 1):

Met—Ser—Thr—Asn—Pro—Lys—Pro—Gln—Arg—Lys—
Thr—Lys—Arg—Asn—Thr—Asn—Arg—Arg—Pro—Gln.

3. The kit of claim 2 further comprising a support to which said peptide is bound.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

```
Met  Ser  Thr  Asn  Pro  Lys  Pro  Gln  Arg  Lys  Thr  Lys  Arg  Asn  Thr  Asn
 1              5                        10                       15

Arg  Arg  Pro  Gln
            20
```